United States Patent [19]

Sturgill et al.

[11] Patent Number: 5,170,792

[45] Date of Patent: Dec. 15, 1992

[54] ADAPTIVE TISSUE VELOCITY COMPENSATION FOR ULTRASONIC DOPPLER IMAGING

[75] Inventors: Michael R. Sturgill, Phoenix; Richard H. Love, Scottsdale; Marsha A. Thesen, Phoenix; Bradley K. Herres, deceased, late of Scottsdale, all of Ariz.; Theodore F. Herres, executor; Muriel Herres, executor, both of Sterling, Colo.

[73] Assignee: Acoustic Imaging Technologies Corporation, Phoenix, Ariz.

[21] Appl. No.: 616,177

[22] Filed: Nov. 20, 1990

Related U.S. Application Data

[63] Continuation-in-part of Ser. No. 614,258, Nov. 16, 1990, which is a continuation-in-part of Ser. No. 527,565, May 23, 1990, abandoned, which is a continuation-in-part of Ser. No. 441,861, Nov. 27, 1989, abandoned.

[51] Int. Cl.$^5$ .............................................. A61B 8/06
[52] U.S. Cl. ............................ 128/661.09; 128/660.05; 128/661.08
[58] Field of Search ............... 128/660.01, 660.04, 128/660.05, 661.08, 661.09, 661.10; 73/861.25

[56] References Cited

U.S. PATENT DOCUMENTS

| | | | |
|---|---|---|---|
| 4,509,525 | 4/1985 | Seo | 128/661.09 |
| 4,583,552 | 4/1986 | Iinuma | 128/661.09 |
| 4,809,703 | 3/1989 | Ishikawa et al. | 128/661.08 |
| 4,850,361 | 7/1989 | Maekawa | 128/660.04 |
| 4,883,060 | 11/1989 | Pesque et al. | 128/660.01 |
| 4,961,427 | 10/1990 | Namekawa et al. | 128/661.09 |
| 4,993,417 | 2/1991 | Seo | 128/661.09 |
| 5,040,225 | 8/1991 | Gouge | 128/660.04 |

Primary Examiner—Kyle L. Howell
Assistant Examiner—George Manuel
Attorney, Agent, or Firm—Christie, Parker & Hale

[57] ABSTRACT

An ultrasonic blood flow measuring and imaging system comprises a transmit-receive transducer for transmitting ultrasonic pulses toward and into the human body and for receiving reflected echo signals which are then processed for use in a Doppler blood flow imaging and display system. Multiple ultrasonic pulses are transmitted into the body at each of a number for angles in an area under diagnosis. For each angle, a plurality of reflected echo signals are received during successive predetermined time intervals. Each received echo signal has a tissue motion Doppler component representative of reflection from moving tissue and a blood flow Doppler component representative of relfection from both moving tissue and flowing blood. The reflected echo signals are processed in a system which includes tissue velocity determining elements for estimating the velocity of the tissue motion, and tissue velocity canceller elements for removing a tissue velocity component from the received echo signals. The system provides output signals used to produce color flow imaging of the blood flow in the area under diagnosis.

27 Claims, 10 Drawing Sheets

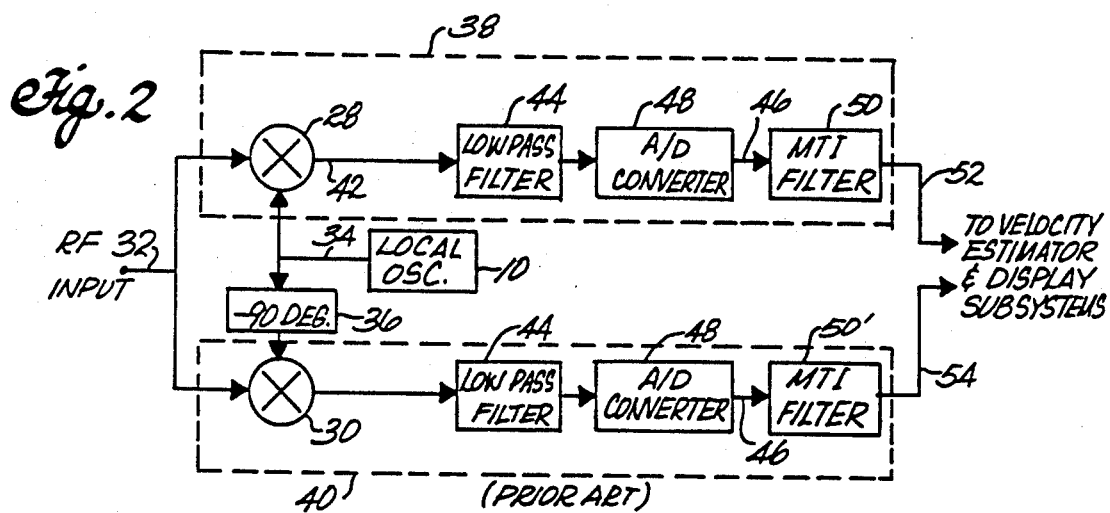
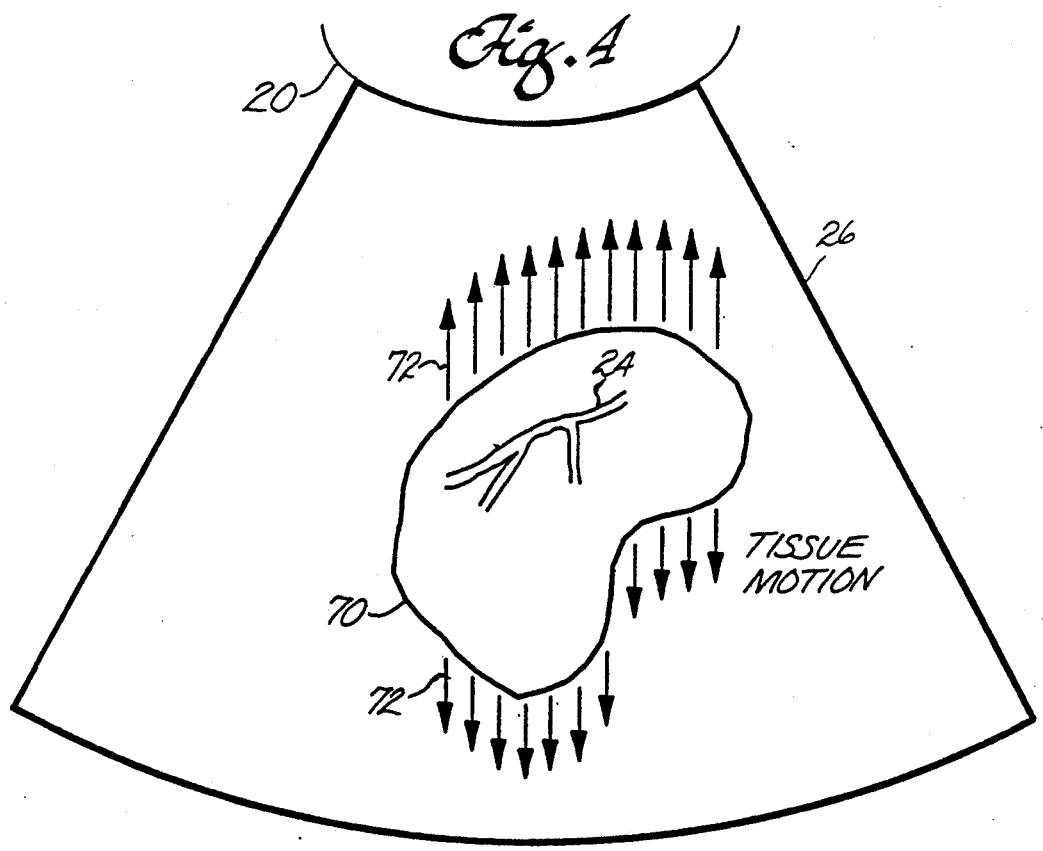

EXAMPLE VELOCITY VECTORS

ADAPTIVE TISSUE VELOCITY COMPENSATION FOR ULTRASONIC DOPPLER IMAGING

CROSS-REFERENCE

This is a continuation-in-part of application Ser. No. 07/614,258, filed Nov. 16, 1990, entitled "Ultrasonic Doppler Imaging Systems With Improved Flow Sensitivity", which is a continuation-in-part of application Ser. No. 07/527,565, filed May 23, 1990, now abandoned entitled "Ultrasonic Doppler Imaging With Analog Feedback Signal Canceller," which is a continuation-in-part of application Ser. No. 07/441,861, filed Nov. 27, 1989, now abandoned, all of which are incorporated herein by this reference.

FIELD OF THE INVENTION

This invention relates to ultrasonic diagnosis techniques, and more particularly, to ultrasonic Doppler blood flow imaging and display systems. The invention is particularly directed to techniques for improving the accuracy of measurement of blood flow velocity in an ultrasonic color flow imaging system in the presence of moving tissue.

BACKGROUND OF THE INVENTION

Various techniques have been used in the past to achieve noninvasive imaging of blood flow using ultrasound. Recent developments in Doppler echocardiography are an example. Although the present invention is applicable to other uses, it will be described below in connection with its applicability to Doppler ultrasound blood flow imaging.

A typical ultrasound blood flow imaging system includes an ultrasonic transmit-receive transducer for transmitting ultrasonic pulses into a region of the body under diagnosis and for receiving echo signals of the transmitted ultrasound waves reflected by blood flowing in the area being scanned. One type of transducer is in the form of a probe containing a curved linear array of piezoelectric elements that insonify a sector shaped area of the body. A typical diagnosis with ultrasound includes scanning the patient with the ultrasound probe to measure blood flow rate in an artery, a vein, or in the heart. A signal processing system processes the received echo signals for measuring the Doppler shift frequency of the echo signals to thereby calculate the velocity of the blood flow, and the result of the velocity distribution measurement is displayed as a Doppler blood flow image. Techniques have been conventionally used for displaying the Doppler shift as a black and white image displaying velocity (B-mode gray scale display of echo amplitudes); in more recent years, color imaging techniques have been developed for displaying the two dimensional velocity distribution of blood flow in the area under diagnosis.

In order to estimate the Doppler shifts of the echoes received from the blood cells, an ultrasonic imaging system commonly transmits several (e.g. 4-16) pulses at one angle in the region under diagnosis and then detects the variations in the phase of the echoes from pulse to pulse.

Echo signal components reflected from stationary targets are removed, while components reflected from very slowly moving (near-stationary) targets such as moving tissue, are, for the most part, only partially removed. These stationary and near-stationary tissue motion signals are referred to as "clutter." Their complete removal is desirable since their relative amplitude is typically orders of magnitude greater than the Doppler-shifted signals resulting from blood flow.

A stationary cancelling filter (also called a moving target indication filter or MTI filter) is used to eliminate signals caused by stationary objects, and to partially eliminate signals caused by near-stationary objects. In a typical MTI filter, echo signals from consecutive sound receptions are subtracted. The subtraction steps eliminate the signal due to stationary tissue and partially eliminate signals due to near-stationary tissue. The MTI filter output is then processed by a velocity estimator to extract the Doppler frequency information, which is converted to velocity data signals suitable for display in color or on a B-mode gray scale display of echo amplitudes.

Ideally, the extracted Doppler frequency information contains only those Doppler signal components representing blood flow. In practice, however, this information also includes components representing moving tissue, which are not removed by the MTI filter. Such tissue motion may be due to breathing, heartbeat, probe motion, or the like. In general, the relative amplitude of the signals due to tissue motion is orders of magnitude greater than the signals representing blood flow. The typical MTI filter will not cancel all of these signals because they are not completely stationary. When sufficient tissue motion occurs, a color smear appears over the velocity display image, making it difficult to discriminate between actual blood flow and tissue movement artifacts. This is so because the blood flow information which is sought is obscured by the color induced by tissue motion.

The present invention is concerned with improving the accuracy of blood flow estimation of a Doppler color flow imaging system. This objective is achieved by providing a technique for estimating tissue velocity, and for cancelling this velocity component from the Doppler frequency signals to produce a blood flow signal compensated for the errors produced by tissue motion.

SUMMARY OF THE INVENTION

The present invention provides a tissue velocity estimator for estimating the velocity of tissue motion in echo signals in an ultrasound flow imaging system, and a tissue velocity canceller for removing a tissue velocity component from the echo signals to provide accurate blood flow image data signals.

Briefly, the invention includes an ultrasonic wave transmitting and receiving device for sequentially transmitting ultrasonic waves toward and into a living body over a predetermined time interval and for receiving their reflected echo signals. In each flow measuring sequence, a series of ultrasound signals in the form of pulse echo sequences, each representing an acoustic line, are transmitted toward and received from a selected location under diagnosis at a selected angle over a predetermined time interval. Each received echo signal has a tissue motion Doppler component representative of reflection from moving tissue and a blood flow Doppler component representative of reflection from both moving tissue and flowing blood. The echo signals received during successive predetermined time intervals are processed by signal processing means which include (i) tissue velocity determining means for estimating the velocity of the tissue motion, and (ii) tissue velocity canceller means for removing a tissue velocity component from the received echo signals. The output signals from the tissue velocity canceller means are processed to generate therefrom Doppler flow image data signals for use in imaging the blood flow.

In a preferred form of the invention, the tissue velocity determining means includes memory means for storing multiple reflected echo signals during each time interval. Also included are detector means responsive to the memory means for discriminating between those components of the echo signals representative of tissue motion and those representative of the combination of tissue motion and blood flow. A tissue velocity estimator responsive to the detector means provides a tissue velocity signal indicative of tissue velocity The frequency of the tissue velocity signal is related to the frequency of the tissue motion Doppler component of the echo signals.

The tissue velocity canceller includes a demodulator responsive to the tissue velocity signal and the received echo signals to demodulate the echo signals in a manner which translates the frequency spectrum of the echo signals such that the frequency of the demodulated tissue motion Doppler component of the echo signals is substantially at a baseband frequency. The canceller further includes an MTI filter responsive to the demodulator output for removing from the demodulated echo signals those components substantially at the baseband frequency, whereby the MTI filter output signal is compensated for errors resulting from tissue motion and is substantially representative of the velocity of blood flow. The filter output signal is provided to a velocity estimator and display system to thereby produce Doppler flow image data for use in color imaging of blood flow velocity in the area under diagnosis One advantage of this invention is that it produces a more accurate estimate of blood flow velocity than prior art systems, with a resultant higher quality color imaging display.

These and other aspects of the invention will be more fully understood by referring to the following detailed description and the accompanying drawings

BRIEF DESCRIPTION OF THE DRAWINGS

FIG. 2 is a functional block diagram illustrating a prior art Doppler signal processor for an ultrasonic imaging system;

FIG. 4 is a schematic representation of a blood vessel in a body organ scanned by a transducer in the measuring system of FIG. 1, showing an example of tissue motion as a result of breathing;

DETAILED DESCRIPTION

Figure 1:
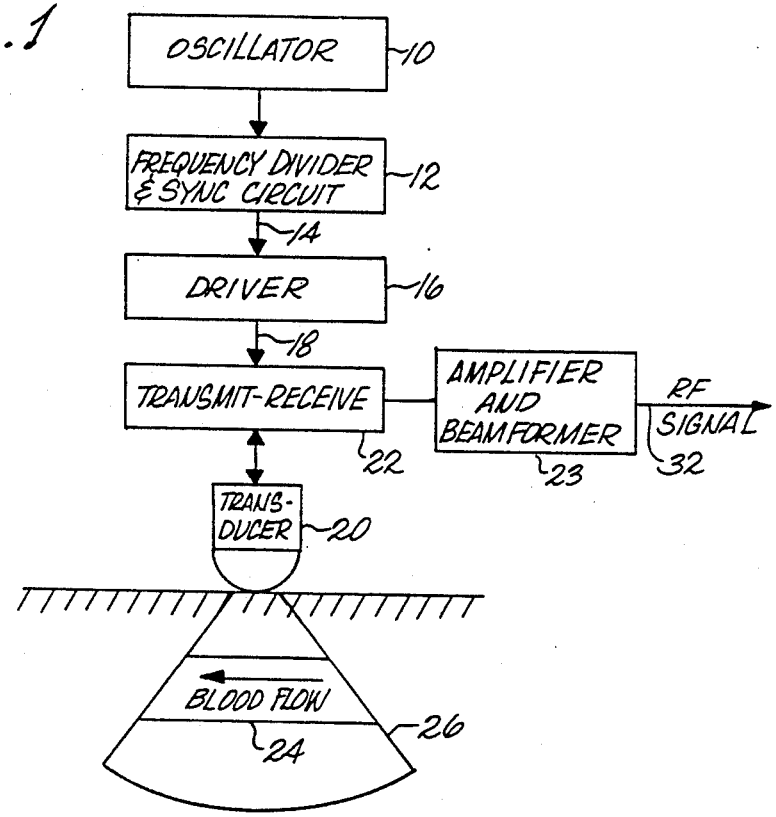
FIG. 1 is a schematic functional block diagram illustrating components of a blood flow measuring system for producing input signals to the systems shown in FIGS. 2, 9 or 12.
Figure 3:
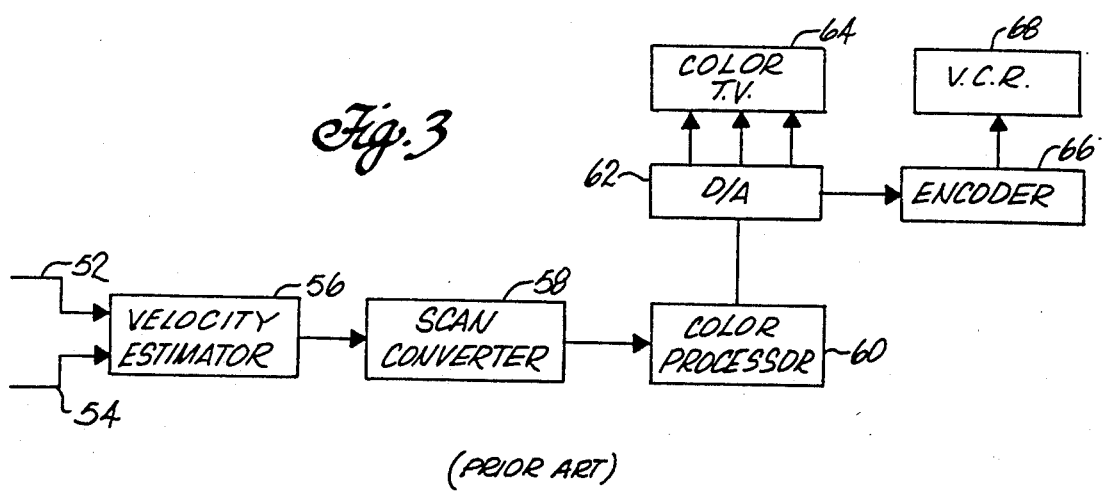
FIG. 3 is a functional block diagram illustrating a velocity estimator and display subsystem for conventional processing of the information produced by the systems shown in FIGS. 2, 9 or 12.
Figure 9:
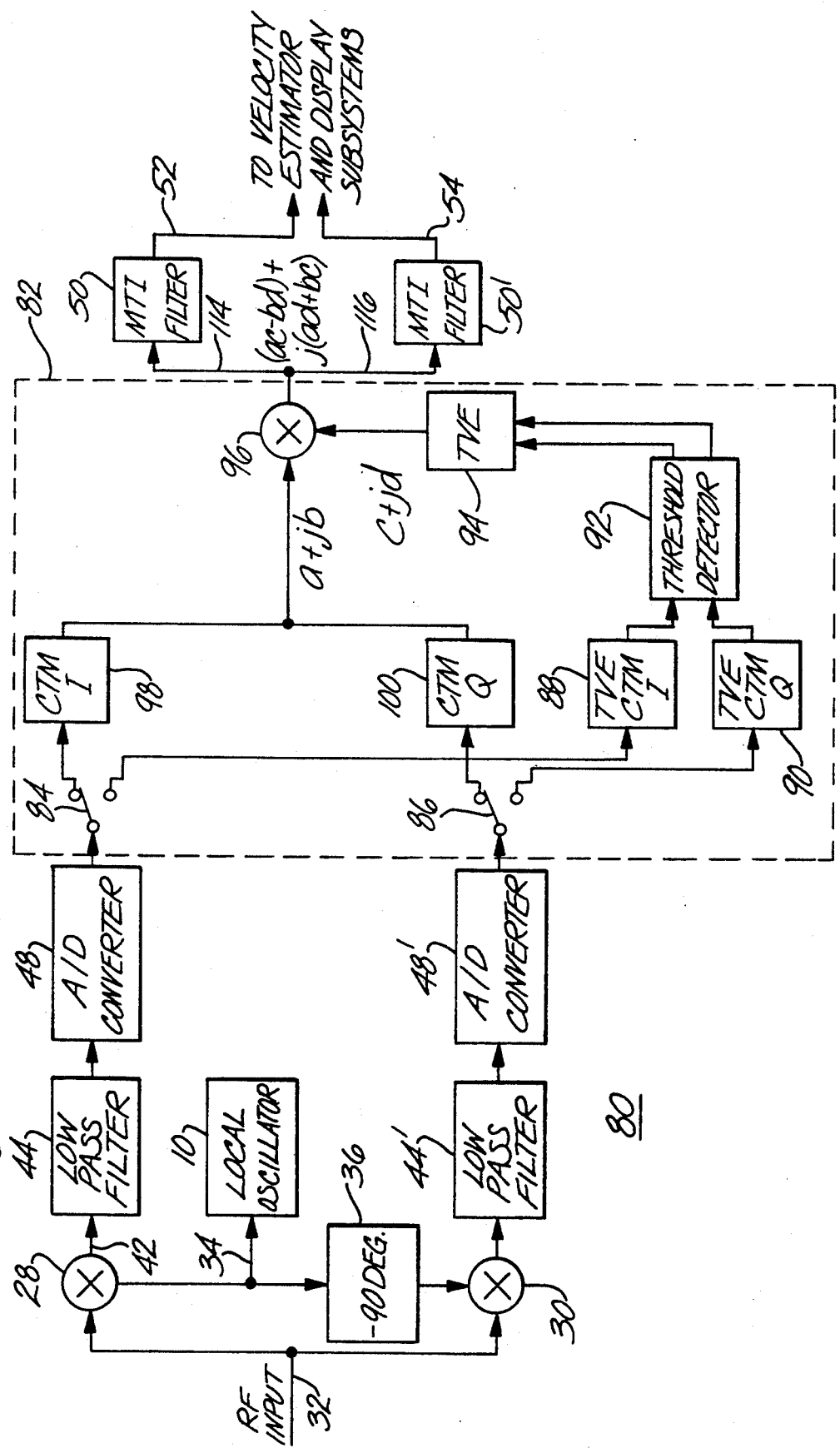
FIG. 9 is a functional block diagram of a Doppler signal processor in accordance with a first embodiment of the present invention.
Figure 12:
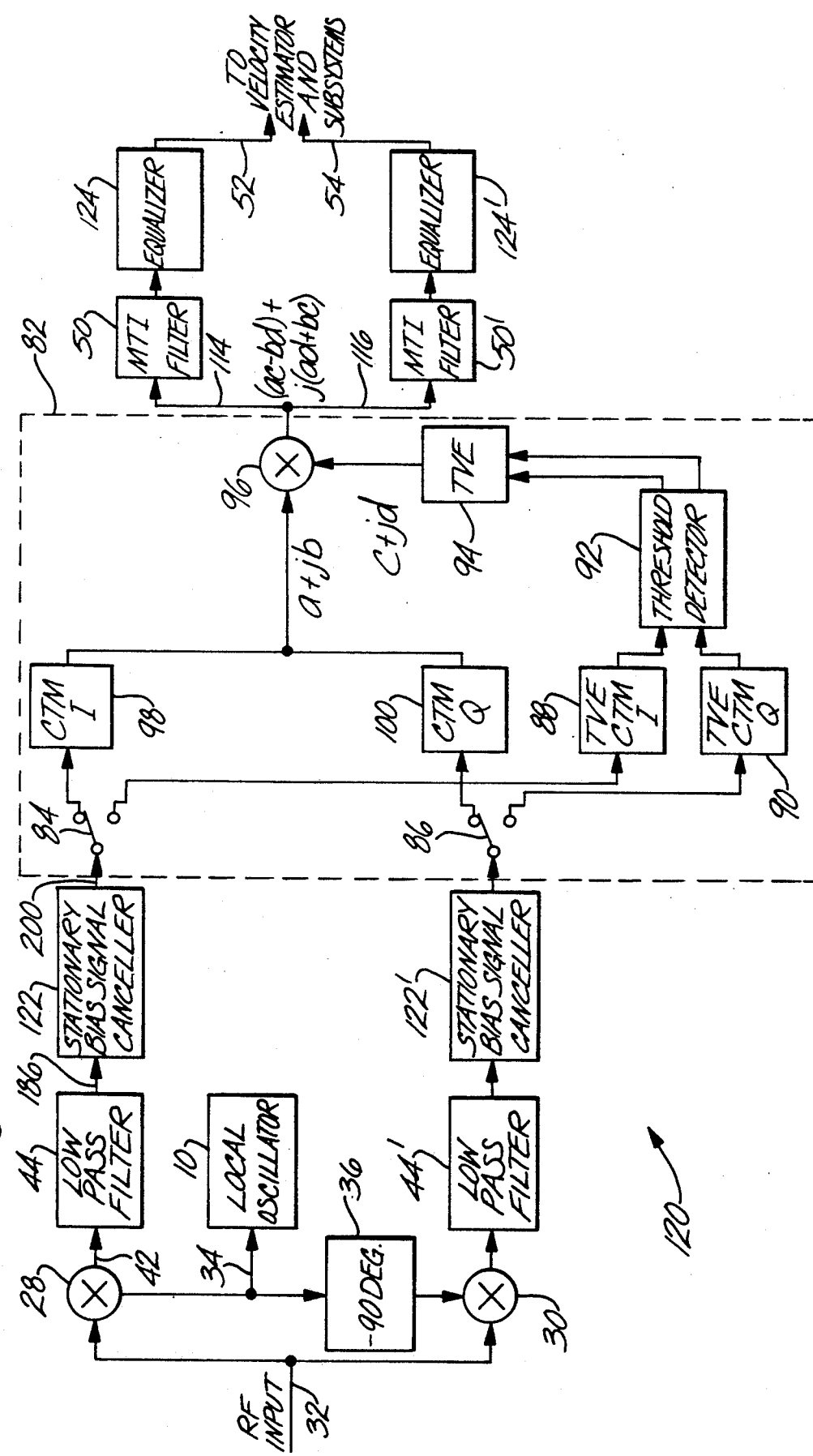
FIG. 12 is a functional block diagram of a Doppler signal processor in accordance with a second and preferred embodiment of the present invention.

Referring to the drawings, FIGS. 1 and 3 illustrate conventional components of a blood flow measuring and imaging system. FIG. 2 illustrates components of a prior art Doppler signal processor for ultrasonic flow imaging. FIG. 1 is an example of one means for producing input signals to the FIG. 2 system, and FIG. 3 illustrates one type of velocity estimator and display subsystem for processing and displaying output signals from the prior art system of FIG. 2. As described below, FIGS. 9 and 12 illustrate components of Doppler signal processors constructed according to principles of this invention. The processors of FIGS. 9 and 12 can also be used in conjunction with the input signals derived from the system of FIG. 1, and with the velocity estimator and display subsystem shown in FIG. 3.

Referring now to FIG. a blood flow measuring system includes an oscillator 10 which generates a stable high frequency oscillation signal applied to a frequency-dividing and synchronizing circuit 12. In response to the high frequency oscillation signal, the circuit 12 generates a digital pulse signal 14 for ultrasonic pulse beam transmission. In response to the digital pulse signal 14, a driver circuit 16 applies an analog pulse signal 18 to a probe 20 through a transmit-receive changeover circuit 22. The probe 20 is excited to transmit an ultrasonic pulse beam toward a blood vessel 24 in a sector 26 of a living body under examination.

The probe 20 may be a curved linear array of the type disclosed in Plesset et al. U.S. Pat. No. 4,409,982. The beam of the probe 20 repeatedly steps through successive angles that scan the entire sector 26. During each such scan of the entire sector, the data to display one frame is acquired. Each angle at which the beam points corresponds to one "color flow line" of the sector display. At each angle, a plurality of n pulses, where n is typically between 4 and 16, are transmitted from the probe 20 and the echos are received and Doppler processed. One "acoustic line" of data is acquired for each pulse transmission. (The value of i.e., the number of acoustic lines in a flow line, is selected by the equipment operator, depending upon the desired resolution and frame rate—the larger n, the lower the frame rate and the higher the velocity resolution.)

From n acoustic lines of data, one color flow line is derived. The beam then steps to the next angle in succession and n pulses are again transmitted from the probe 20 and the echos are received and Doppler processed to derive another flow line. During Doppler processing, each transmitted pulse is sampled a relatively large number of times, e.g. up to 256 times, at successive time intervals after pulse transmission to define sample cells along the direction of the beam. The number and location of the sample cells relative to the probe 20 are selected by the equipment operator to permit diagnosis of the desired region of interest. The velocity in the region along the beam direction corresponding to each of the selected cells is calculated from the samples for that cell derived from the echos from the n transmitted pulses.

The signal reflected from the blood vessel 24 is converted by the probe 20 into an electrical signal, and this signal is applied, through the transmit-receive changeover circuit 22, to a high frequency amplifier and beamformer 23 that focuses the reflected signal. The amplified output signal is applied to quadrature detectors (balanced mixers) 28 and 30 in the ultrasound signal processing system illustrated in FIG. 2. The signals derived from the transducer and input to the quadrature channels at 32 may be RF or IF; use of an RF beamformer signal is a preferred embodiment. The beamformer could comprise the beamformer disclosed in application Ser. No. 07/415,404, filed Sep. 29, 1989, the disclosure of which is incorporated fully herein by reference. The described Doppler processing circuitry could be connected in parallel with the video processor of the referenced application in the diagram of its FIG. 1.

The oscillator 10 generates and applies a stable high frequency signal to the synchronizing circuit 12 which generates various output signals having a desired frequency. These output signals include a signal for causing repeated transmission of an ultrasonic pulse beam. This signal is applied through the changeover circuit 22 to the ultrasound probe 20, and the piezoelectric elements contained in the probe are excited to transmit an ultrasonic pulse beam toward and into the internal moving part of the living body under diagnosis. The internal moving part is, in this example, blood flow in the blood vessel 24. The sector 26 designates a region of scanning for the measurement of a Doppler blood flow image. A transmitter control circuit controls the ultrasonic pulse beam to transmit it at predetermined scanning angles, direction and depth toward and into the sector 26. Pulses of the transmitted ultrasonic beam reflected from the various tissue interfaces in the body sector are received by the ultrasonic probe. The received echo signal 32, after being amplified and focused by the RF amplifier and beamformer 23, is then sent to the processing system of FIG. 2 for further processing.

In order to estimate the Doppler shifts of the echoes received from blood cells, an ultrasound imaging system must transmit several (e.g. from 4 to 16) pulses at one angle and then detect the variations in the phase of the echoes from pulse to pulse at different depths. The echos from these pulses are range gated to define the same number of cells at different depths from the probe. The frequency shift of each range gated echo represents the velocity in the corresponding cell. Part of the conventional receiving process is shown in FIG. 2.

A quadrature baseband detection process is used in which, in this example, the RF input signal 32 from the beamformer 23 of FIG. 1 is applied to the mixers 28 and 30. Separately, the reference signal 34 from the oscillator 10 is applied to the mixers, with the reference signal sent to one mixer 30 having its phase shifted 90° by a phase shift circuit 36, so that a 90° phase-shifted reference signal is applied to the mixer 30, together with the amplified echo signal 32 from the beamformer. The reference signal 34 applied to the mixer 28, in the description to follow, is processed as part of an in-phase channel 38; and the phase-shifted signal is processed in a separate quadrature channel 40 having system components similar to the in-phase channel. Therefore, the description to follow will suffice for both channels.

The outputs of the balanced mixers 28 and 30 are analog signals representing the product of the input echo signal 32 and the input reference signal 34. The analog signal 42 is then amplified by a first amplifier, passed through a low-pass filter 44, and then amplified by a second amplifier. In the illustrated embodiment, the RF signal from the receiving beamformer is down-converted to a baseband frequency in the quadrature channels, using the balanced mixers. A swept gain function was previously applied to the RF signal to compensate for ultrasound attenuation in tissue. The first amplifier is a fixed gain stage. The low-pass filter 44 sets the detection bandwidth which can be between about 100 KHz and about 2.5 MHz.

The output signal from the second amplifier is then converted to a digital output signal 46 in an analog-to-digital converter 48 for processing in an MTI filter or stationary canceller 50 to cancel stationary components of the received echo signals. Echoes from stationary, or nearly stationary structures in the body are much stronger than the echoes from blood cells, often by as much as 60 dB. The analog-to-digital converter 48 has a large dynamic range in order to keep the blood flow signals well above quantization noise and yet not saturate on the stationary signals. The MTI filter 50 is used to remove stationary, or slowly moving components after the signal has been converted to digital by the analog-to-digital converter 48. The filter can have a comb response with notches at the pulse repetition frequency and its harmonics The MTI filter output signals 52 and 54 from the quadrature channels can be processed by the system of FIG. 3 to extract the Doppler frequency information, at discrete ranges, either by an autocorrelation technique, or by a frequency domain processing system, such as by fast Fourier transform (FFT) techniques.

FIG. 3 illustrates components of a conventional system for further processing and imaging of the Doppler ultrasound blood flow information derived from the system shown in FIG. 2. The baseband information 52 and 54 is digitally processed in a velocity estimator 56 and a digital scan converter 58 and is then sent to a color processor 60 for further digital processing of the information. The results are converted by a digital-to-analog converter 62 into analog signals representing the three primary colors, red, green and blue, which are displayed on the CRT of a color TV monitor 64. The output signals also can be converted into standard TV signals via an encoder 66 for connection to peripheral equipment such as a VCR 68.

One shortcoming of the Doppler signal processor system of FIG. 2 is that the MTI filters 50, 50' do not remove from the received Doppler signals the components representing moving tissue, because these components are not completely stationary. Accordingly, the output signals appearing on the lines 52 and 54 contain components representing moving tissue as well as components representing the combination of moving tissue and blood flow. These components are more clearly seen from the schematic diagrams of FIGS. 4 and 5.

FIG. 4 shows anatomically the motions which may occur in the sector 26 of the body under diagnosis. In general, the Doppler frequency shift from the blood flow (measured by the signal scattering effect of the blood) within a blood vessel 24, where the vessel 24 is within an organ 70, is biased and partially obscured by the motion of the tissue surrounding the vessel (for example, due to breathing), as represented by arrows 72. Since a Doppler frequency shift measurement is made as a result of reflected components of the scatterers in the direction of the wavefront of the interrogating ultrasonic pulses from the probe 20, the component due to tissue motion directly affects the velocity estimate of the blood flow.

When measuring the velocity of blood within a vessel which is inside moving tissue, the combined velocity, in a vector sense relative to the probe, is given by $$V_{Combined} = V_{Blood} + V_{Tissue} \quad (1)$$

where the summation is a vector summation. This then implies that the blood velocity is given by $$V_{Blood} = V_{Combined} - V_{Tissue} \quad (2)$$

Figure 5:
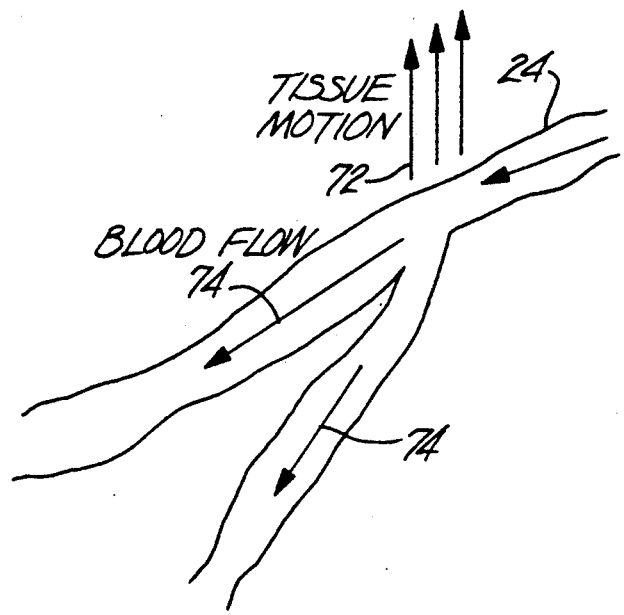
FIG. 5 is an expanded view of the blood vessel of FIG. 4 showing the tissue motion and blood flow velocity components.
Figure 6:
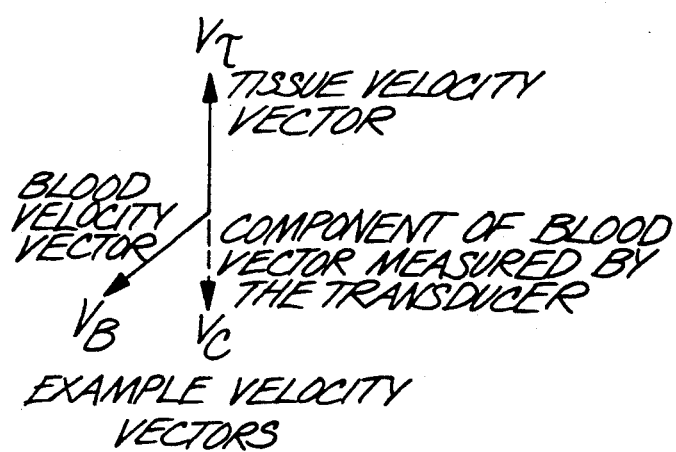
FIG. 6 is a vector diagram showing the velocity vectors as a result of tissue motion and blood flow and also showing the component of the blood vector measured by the transducer in the system of FIG. 1.
Figure 7:
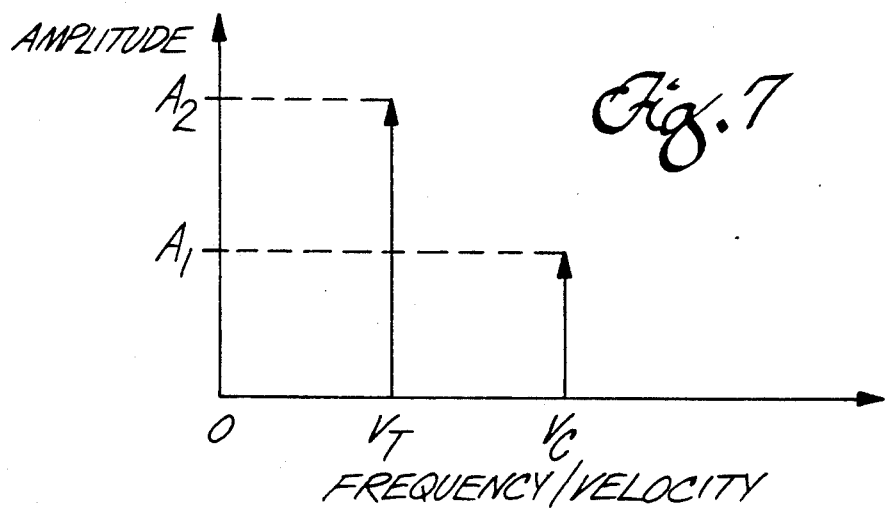
FIG. 7 is a plot of amplitude versus Doppler frequency, showing the tissue motion component and the blood flow component of the Doppler echo signals received by the transducer in the system of FIG. 1 in response to tissue motion and in response to the combination of tissue motion and blood flow, respectively.

FIG. 5 is an expanded View of the blood vessel 24 of FIG. 4, showing the vector components 74 of the blood scatterers within the vessel 24 and the components 72 due to tissue motion. FIG. 6 shows the summation of these components in the direction of the interrogating wavefront from the probe 20, where $V_B$ represents the blood velocity vector, $V_T$ represents the tissue velocity vector, and $V_c$ represents the combination of tissue velocity and blood velocity as measured by the probe 20. FIG. 7 is a plot of the velocity vectors $V_T$ and $V_c$ as they might appear on a graph of amplitude versus Doppler frequency (normalized so that zero represents zero velocity, corresponding to the baseband frequency).

Figure 8:
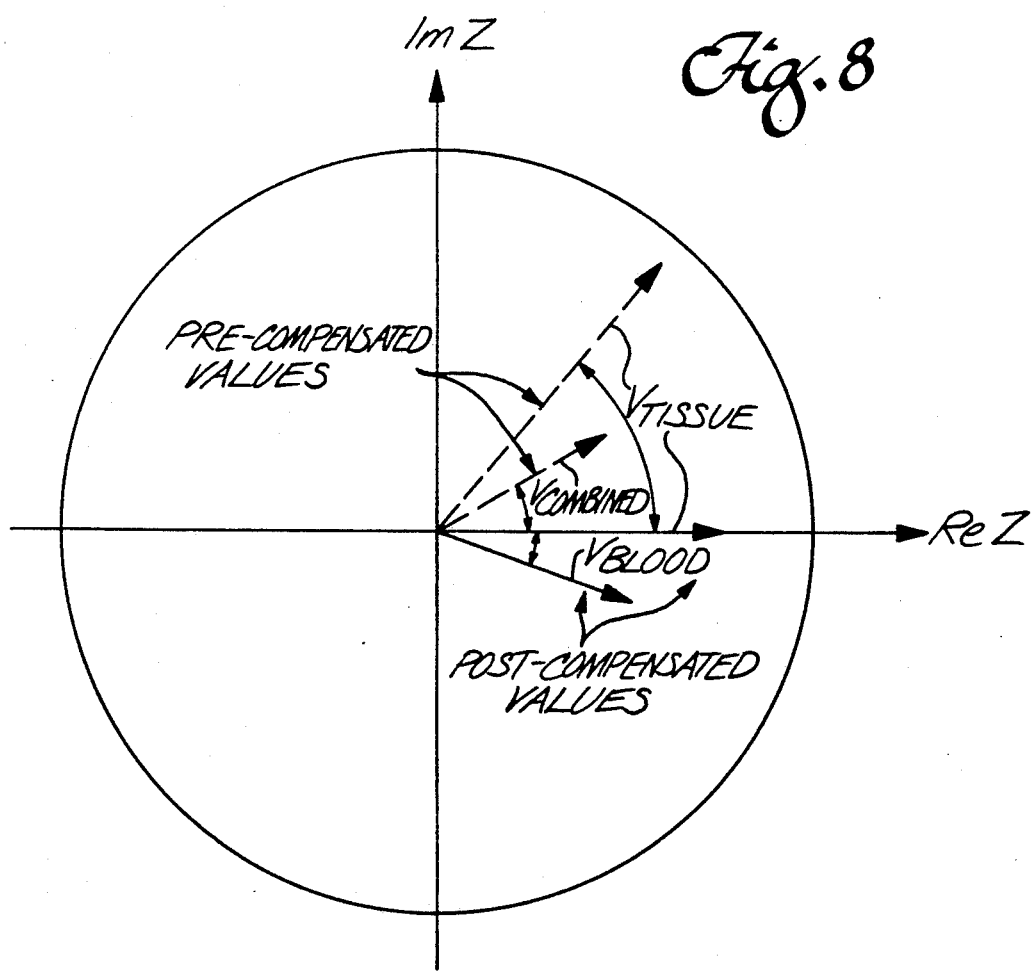
FIG. 8 is a complex frequency domain diagram showing the position of the velocity vector Doppler signals due to tissue motion and due to the combination of tissue motion and blood flow, both before and after being processed by the systems of the present invention.

FIG. 8 shows by dotted lines the velocity vectors $V_T$ and $V_C$ as they would appear in the complex frequency plane. The solid lines in FIG. 8 represent the resulting velocity vectors after the Doppler signals have been processed by the tissue velocity compensation system of the present invention as disclosed at length below.

FIG. 9 is a functional block diagram of a Doppler signal processor system 80 constructed in accordance with a first embodiment of the invention. Comparing FIG. 9 with FIG. 2, it may be seen that the system 80 includes a tissue velocity estimation and compensation subsystem 82 inserted between the analog-to-digital (A/D) converters 48 and the MTI filters 50, 50' in both the in-phase and quadrature channels.

Figure 10:
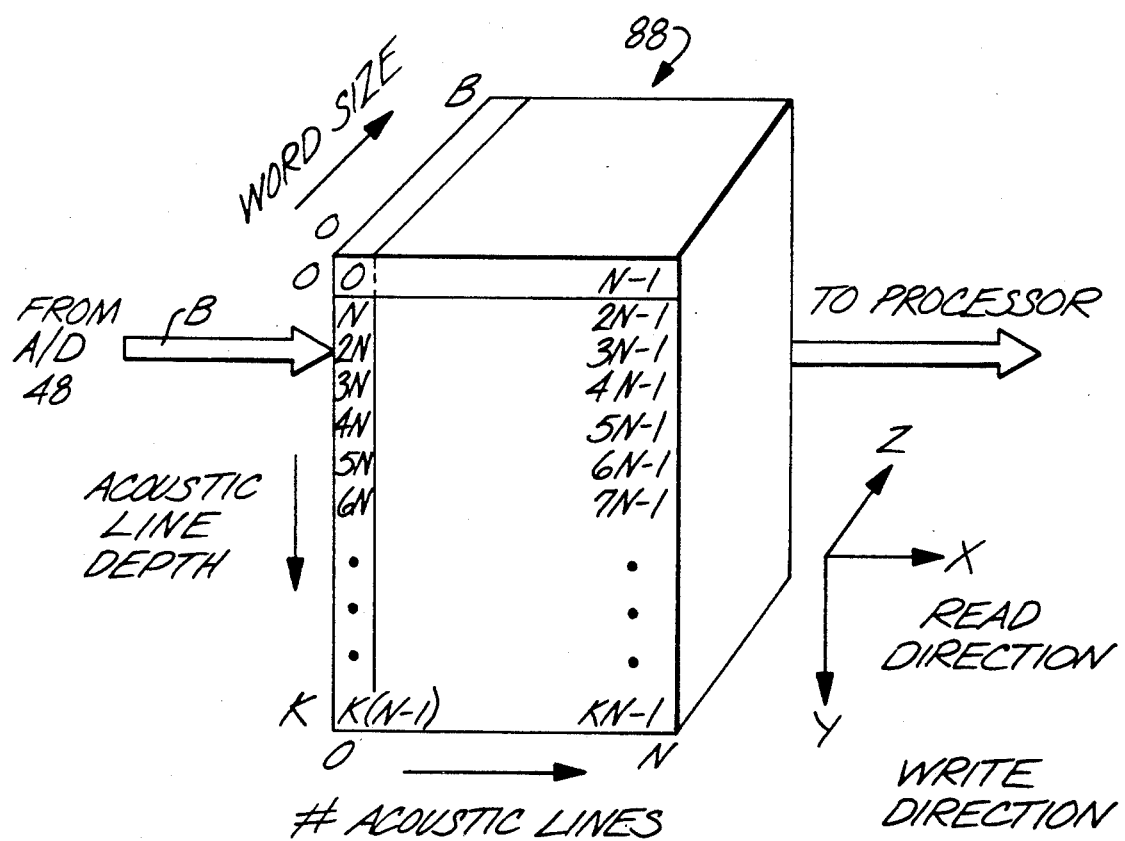
FIG. 10 is a schematic diagram illustrating operation of a corner-turning memory used in the systems shown in FIGS. 9 and 12.

The in-phase Doppler echo signals from the A/D converter 48 are applied to a switch 84 and the quadrature Doppler echo signals from the A/D converter 48' are applied to a switch 86. The switches 84, 86 act to place the system either in a tissue velocity acquisition mode or in a Doppler signal acquisition mode. During the tissue velocity acquisition mode, the switches 84, 86 are placed in the down position (opposite to that shown in FIG. 9) so that the in-phase and quadrature echo signals are provided as inputs to tissue velocity corner turning memories 88 and 90, respectively. A typical corner turning memory (CTM) such as CTM 88 is schematically illustrated in FIG. 10.

In essence, a CTM is an element for storing three-dimensional data arrays. The CTM comprises a two-dimensional scan and corner-turning random access memory having K rows by N columns by B bits deep, in which vertical is the write direction and horizontal is the read direction. Data from each acoustic line are written into a separate column of the memory and data from an acoustic line at a later time interval are written into a second column, and so forth. Each row N contains the data for one sample cell. Data read from any given row N give the data samples for a given volume in space.

Returning to FIG. 9, during the tissue velocity acquisition mode, the CTMs 88 and 90 are used to store the data from the first two acoustic lines during the processing of the n acoustic lines which construct a color flow line. This stored data are provided to a threshold detector 92 the purpose of which is to set an amplitude threshold by comparing the amplitude of the stored data to that of a user adjustable threshold level. Only those data which exceed the threshold level are provided by the detector 92 as inputs to a tissue velocity estimator (TVE) 94.

The tissue velocity estimator 94 may be similar in construction to the above described velocity estimator 56 of FIG. 3 in which conventional autocorrelation or frequency domain processing techniques are used to provide an output signal which is an estimate of velocity. Alternatively, the TVE 94 may be constructed using the techniques disclosed in copending application Ser. No. 07/441,787, filed Nov. 27, 1989, entitled "Maximum Entropy Velocity Estimator for Ultrasonic Flow Imaging System" (now U.S. Pat. No. 5,107,841), incorporated herein by this reference. The output of the TVE 94 is provided as one input to a complex multiplier 96.

After the CTMs 88, 90 have stored the data from the first two acoustic lines (derived from the first two ultrasonic pulse-echo sequences), the system 80 switches into the Doppler signal acquisition mode. This is accomplished by a suitable counter (not shown) which causes the switches 84, 86 to switch to the positions shown in FIG. 9 after the data from the two acoustic lines have been acquired. With the switches in the position shown, the in-phase and quadrature data from the succeeding n−2 acoustic lines of the flow line are provided to corner turning modules 98 and 100, respectively. The outputs from these CTMs are provided as an additional input to the complex multiplier 96.

Figure 11:
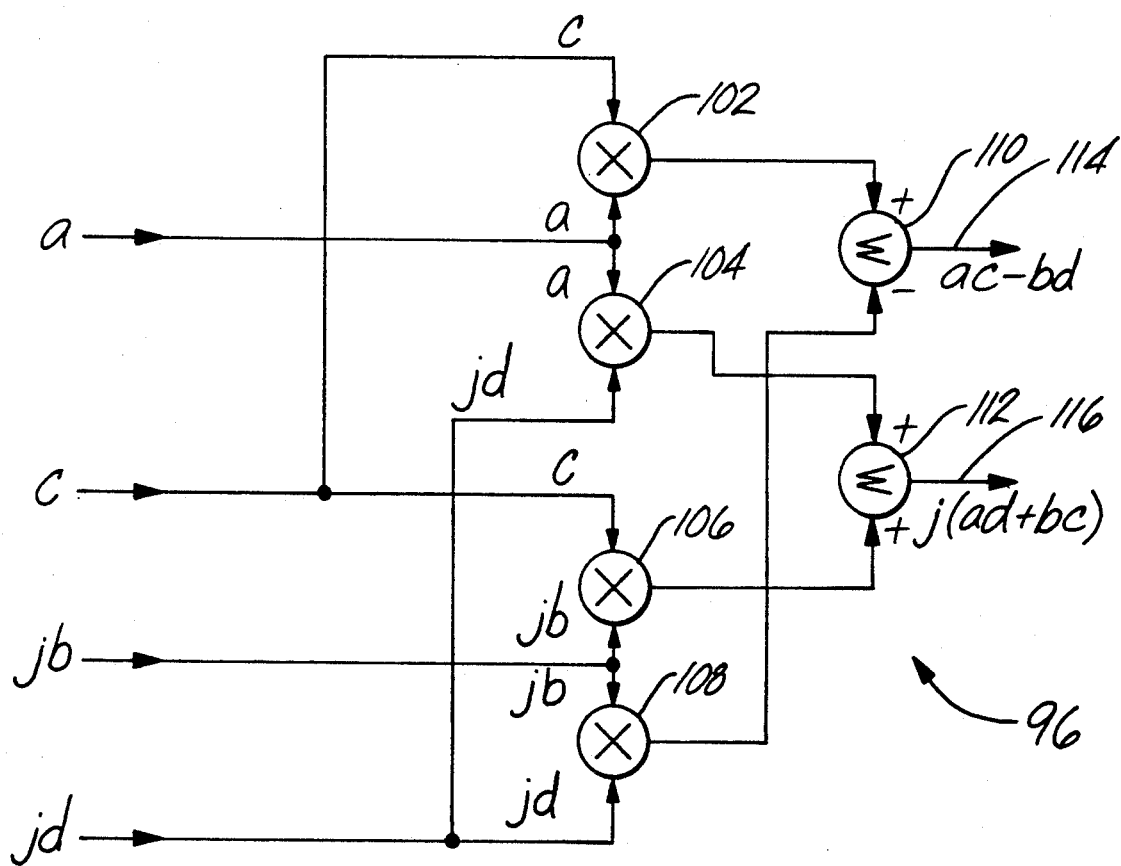
FIG. 11 is a functional block diagram of a complex multiplier used in the processor systems shown in FIGS. 9 and 12.

The complex multiplier 96 acts as a demodulator which shifts the frequency of the signal from the CTMs 98, 100 by an amount determined by the frequency of the signal from the TVE 94. One embodiment of the multiplier 96 is schematically illustrated in FIG. 11, where the signal from the CTMs 98, 100 is represented by the complex expression $a+jb$ and the signal from the TVE 94 is represented by the complex expression $c+jd$.

The real coefficients a and c and the imaginary coefficients jb and jd are multiplied in the arrangement shown by multipliers 102, 104, 106 and 108, and then added by adders 110 and 112 to produce an in-phase output signal equal to ac−bd and a quadrature output signal equal to j(ad+bc). The in-phase output signal is provided on line 114 to the MTI filter 50, and the quadrature output signal is provided on line 116 to the MTI filter 50'. The outputs of the MTI filters 50, 50' are provided to the velocity estimator and display subsystems of FIG. 3 as described above.

The operation of the system 80 is as follows. The pulse echo data from the probe 20 is demodulated, filtered and converted to digital by the elements 28, 30, 44, 48 and 48' as described above. The data from the first two acoustic lines in a flow image line sequence on n acoustic pulses are processed by the system 80 in the tissue velocity acquisition mode. In this mode, the data from these two acoustic lines are stored in CTMs 88 and 90. Storing the data from two successive ultrasonic pulses enables velocity information to be extracted therefrom. The data thus stored contains amplitude and frequency information representing both the $V_T$ (tissue velocity) vector and the $V_C$ (combined blood and tissue velocity) vector.

As shown in FIGS. 7 and 8, the amplitude of the $V_T$ vector is generally substantially larger than that of the $V_C$ vector. This characteristic is used to advantage by the threshold detector 92, which acts to discriminate between the $V_T$ and the $V_C$ vectors on the basis of amplitude. The system user adjusts the threshold level of the detector 92 in an adaptive fashion until the flow image display indicates proper system operation, as described below.

The proper setting of this level to distinguish between the two vectors would be a setting above the peak amplitude of the $V_C$ vector and below the peak amplitude of the $V_T$ vector. At this setting, only the signal representing the $V_T$ vector is provided to the tissue velocity estimator 94. Accordingly, the TVE 94 provides a signal c+jd to the complex multiplier 96 which is an estimate of the frequency (and hence the velocity) of only the vector $V_T$. The system operator can adjust the setting while viewing the display 64 to determine proper system operation.

At the completion of the tissue velocity acquisition mode, the system 80 switches to the Doppler signal acquisition mode, where the Doppler signals from the succeeding n−2 acoustic pulses are processed. These signals, which contain amplitude and frequency information representing both the $V_T$ (tissue velocity) vector and the $V_C$ (combined blood and tissue velocity) vector are stored in CTMs 98 and 100 and are sequentially provided as signal a+jb to the complex multiplier 96. The multiplier 96 acts as a demodulator to shift the frequency of the signal a+jb by an amount equal to the frequency of the signal c+jb provided by the TVE 94. Since the signal from the TVE 94 is substantially at the frequency of the vector $V_T$, the frequency of the Doppler signal a+jb is shifted by that amount, which has the effect of shifting the frequency spectrum of the signal a+jb such that the portion of that signal representing $V_T$ is shifted to the baseband frequency, representing zero velocity. This frequency shift also has the effect of placing the portion of the signal a+jb representing the vector $V_C$ at a frequency which corresponds to only the blood flow velocity, effectively removing the effect of tissue velocity from that combination vector.

The above described frequency shift effect can be seen graphically by referring to FIG. 8, where the solid lines represent the positions of the vector components of the signals after being processed by the complex multiplier 96. It may be seen that the vector $V_T$ has been shifted to the real axis, representing zero velocity (baseband frequency), and the resultant vector $V_C$ now is equivalent to the desired blood velocity vector $V_B$. The resultant frequency-shifted signal from the multiplier 96, represented by the expression (ac−bd)+j(ad+bc), is filtered by the stationary cancellers or MTI filters 50, 50', which act to remove zero velocity signals. Since the vector $V_T$ has now been shifted to baseband, it is removed by the MTI filters. Accordingly, the signals provided on lines 52, 54 to the blood flow velocity estimator and display subsystems are substantially representative of only the blood flow velocity, the tissue velocity components having been previously removed. It should be noted that the first two acoustic lines used for the tissue velocity acquisition mode are not processed by the velocity estimator 56. As shown below, the data from an additional acoustic line is used to initialize the delay element in the MTI filters.

One significant benefit of the present invention is the substantial elimination of tissue velocity error to enable a more accurate display of blood flow velocity magnitude. This error elimination is accomplished by using the data from only two acoustic lines, thus imposing only a small reduction in image frame rate. It has been found that the tissue velocity sample provided by the data from only two acoustic lines is sufficiently accurate to be used to provide substantial elimination of tissue velocity error for the entire flow line.

Another significant benefit of the present invention may be seen by referring to FIG. 8, which shows how tissue motion can effect the apparent direction of blood flow. The pre-compensated vector $V_C$ in the example shown lies above the real axis, corresponding to a first blood flow direction, while the compensated vector $V_B$ lies below the real axis, indicating the real direction of blood flow is in a second and opposite direction. Thus, tissue motion can actually bias the blood flow estimate enough to indicate a false flow reversal, a problem which is substantially eliminated by the present invention.

FIG. 12 is a functional block diagram of a Doppler signal processor system 120 in accordance with a second and preferred embodiment of the invention, which incorporates into the system 80 the analog feedback stationary bias signal canceller and the MTI filter equalizer inventions disclosed in the co-pending applications cross-referenced above. Comparing FIG. 12 to FIG. 8, it will be seen that stationary bias signal cancellers 122 and 122' replace the A/D converters 48 and 48', respectively, and equalizer circuits 124, 124' are inserted following the MTI filters 50, 50'.

Figure 13:
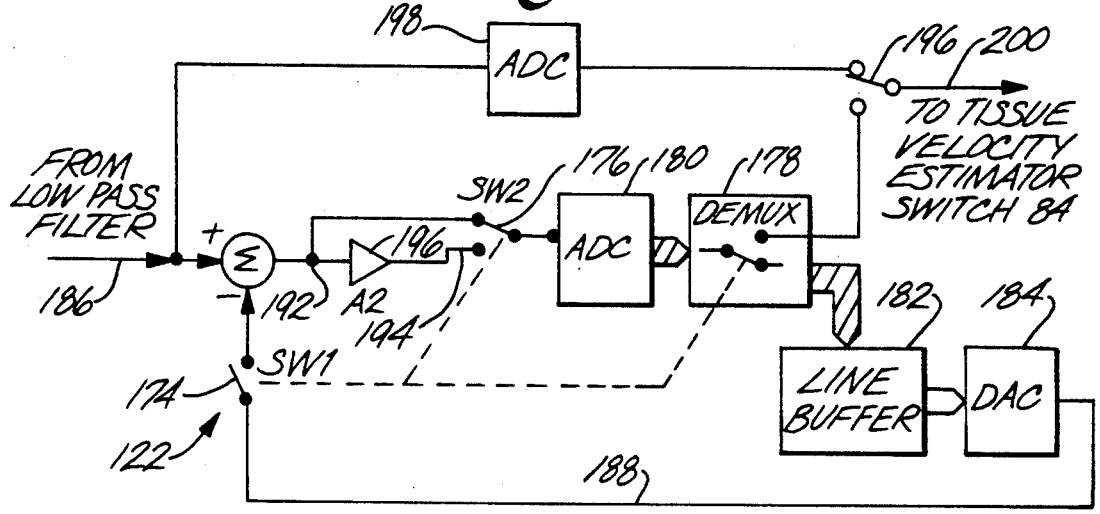
FIG. 13 is a functional block diagram of an analog feedback stationary bias signal canceller used in the processor system shown in FIG. 12.

FIG. 13 is a functional block diagram of the analog feedback stationary bias signal canceller 122 (and 122'). The stationary bias signal canceller 122 operates in two modes: bias signal acquisition and then Doppler signal acquisition. These two modes occur in succession during each flow line data acquisition interval.

Electronic switches 174 and 176 and a demultiplexer 178 are shown in FIG. 13 in the bias signal acquisition mode. An analog-to-digital converter 180, the addresses of a line buffer 182, and a digital-to-analog converter 184 are all clocked at a sample rate determined by the desired resolution of a flow line. This sample rate is typically between about 200 KHz and about 5 MHz. As stated above, in each flow line measuring sequence, a number of ultrasound pulses are directed at a predetermined angle in the body sector 26 under diagnosis. One acoustic line of data is acquired for each pulse transmission.

In the bias signal acquisition mode, a single acoustic line (pulse-echo) is first transmitted and received. The resultant signal is then stored as a stationary bias signal in the line buffer 182, after which the system switches to the Doppler acquisition mode. The stored bias signal can be thought of as representing primarily stationary targets. The acoustic line that was used to acquire the stationary bias signal is not used for flow estimation. On each of the succeeding n pulses which are transmitted along the same angle and toward the same target as part of the flow line, the stored bias signal is recalled from the line buffer 182, converted to analog form by a digital-to-analog converter 184, and subtracted from the incoming signals 186 derived from the echoes from these n succeeding pulses.

During the Doppler acquisition mode, the switch 174 is closed so that the analog signal 188 from the converter 184, representing the stationary bias signal component, is fed back to a summing junction 190 for subtracting this bias signal from the subsequent signals 186. An analog residue signal 192 output from the summing junction 190 contains the pulse-to-pulse variations which principally constitute the Doppler signal. During the Doppler acquisition mode, the switch 176 is closed so that the residue signals 194, which have then been boosted in gain by the second amplifier 196, are then converted to digital in the analog-to-digital converter 180, selected by the demultiplexer 178, and provided to a switch 196.

A suitable counter (not shown) controls the state of switches 74 and 76, demultiplexer 78, and switches 196, 84 and 86 (FIG. 12) to coordinate the two operating modes of the cancellers 122, 122' with the two operating modes of the tissue velocity estimator/compensation system 82 described above, for each flow line sequence. The coordination of these modes is as follows.

As described above, using switches 84 and 86, the tissue velocity estimation system 82 is placed in the tissue velocity acquisition mode for processing the data from the first two acoustic lines of the n acoustic lines which construct a flow line. During the time interval in which the first two acoustic lines are being processed by the system 82, the switch 196 is placed in the position shown in FIG. 13, whereby data is provided for the tissue velocity acquisition mode via line 186 from low pass filter 44 to A/D converter 198 and then through switch 196 to switch 84 via line 200. During this same time interval, the canceller 122 is placed in the stationary bias signal acquisition mode as described above to store the data from the first acoustic line in this flow line sequence. The canceller 122 need only remain in this mode for the interval of time to acquire the data from one acoustic line, at which time the canceller is switched to the Doppler signal acquisition mode.

The switch 196, however, remains in the position shown for the interval of time necessary for the system 82 to acquire the data from the first two acoustic lines. At the end of this interval, the switch 196 is actuated so that Doppler data is now provided on the line 200 from the demultiplexer 178. At the same time, the system 82 is also placed in the Doppler signal acquisition mode. Accordingly, from the start of the third acoustic line each flow line sequence of n acoustic lines, both the canceller and the tissue velocity estimator system 82 are in the Doppler signal acquisition modes, and the data provided to the system 82 is now compensated by removal of stationary bias by the canceller 122. The operation of the canceller 122' for the quadrature channel is the same as the operation of the canceller 122 for the in-phase channel. The above mode switching functions are repeated for each flow line sequence.

Figure 14:
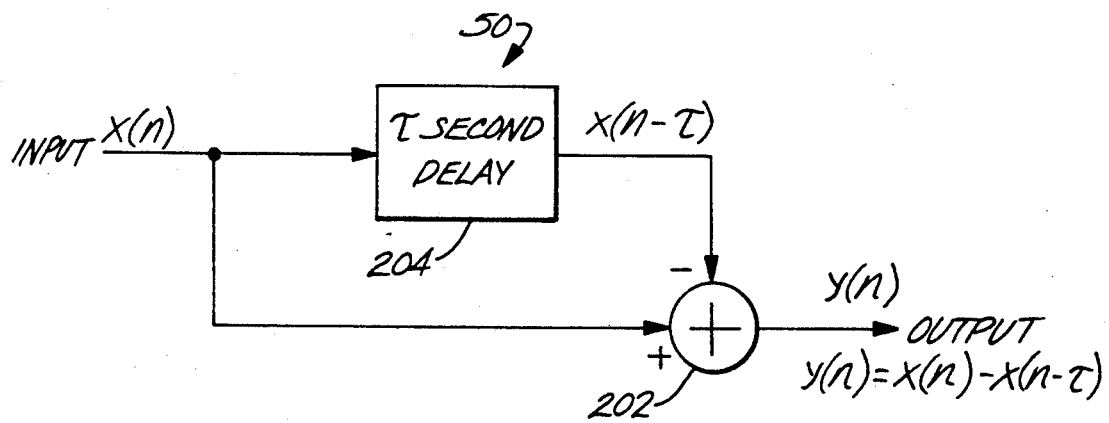
FIG. 14 is a functional block diagram of a conventional MTI filter used in the processors of FIGS. 9 and 12.

By removing the stationary bias from the incoming signals, the circuit gain for processing the resulting Doppler signal 194 may, in general, be boosted substantially by amplifier 196 without overloading the converter 180. This increase in gain results in an improved Doppler signal-to-clutter ratio as a result of the large amplitude Doppler signal, and an increase in the dynamic range of the converter 180, the output signal of which is then processed by the remaining elements of the system 120 to form the blood flow velocity estimate A functional block diagram of a conventional MTI filter 50, 50' is shown in FIG. 14. A purpose of an MTI filter is to provide a means by which stationary objects (zero velocity) are totally attenuated (cancelled) and the remaining information (non-zero velocities) are unattenuated. One problem associated with an MTI filter is in terms of its nonideal characteristics. A characteristic which can be detrimental in measuring slow flows is the frequency response of the MTI filter. Referring to FIG. 14, an input signal x(n) is applied to an accumulator 202 and a delay stage 204 simultaneously. At some time interval ($\tau$) later, the sample previously input to the delay stage 204 becomes x(n−$\tau$) which is an exact replica of the original input, x(n), delayed in time by ($\tau$) seconds. Tau is the reciprocal of the pulse repetition frequency of the pulsed Doppler system. The output of the MTI filter is produced by subtracting the previous sample (taken $\tau$ seconds ago) from the present input sample as shown in FIG. 14.

The output of the MTI filter 50 may be mathematically expressed as $$y(n) = x(n) - x(n-\tau) \quad (3)$$

To evaluate the frequency response of this filter, one first performs a Z transformation on equation (3). This is shown in equations (4) and (5):

$$\begin{aligned} Z\{y(n)\} &= Z\{x(n) - x(n-\tau)\} \\ &= Z\{x(n)\} - Z\{x(n-\tau)\} \end{aligned} \quad (4)$$

$$\begin{aligned} Y(z) &= X(z) - z^{-\tau} X(z) \\ &= X(z)(1 - z^{-\tau}) \end{aligned} \quad (5)$$

The z's in equation (5) are actually a frequency index of the form $z = e^{j\Omega t}$. The $z^{-\tau}$ term in equation (5) represents a delay operator with a delay of $\tau$ seconds. The impulse response of the filter is defined as H(z) and is given in equation (6):

$$H(z) = \frac{Y(z)}{X(z)} = 1 - z^{-\tau} \quad (6)$$

From an analysis of this equation it can be seen that a null in the frequency response occurs at zero velocity. It can also be shown that flows which produce velocities close to zero are also severely attenuated. This attenuated range of flow velocities includes the range of interest for measuring blood flow, and hence produces errors in velocity estimation.

If this frequency response can be altered to produce a flatter gain across the frequency spectrum of interest prior to providing signals for blood flow velocity estimation, the velocity estimator can produce an estimate which is not biased, and hence is more accurate. In general, velocity estimator circuits are designed to operate with signals having a frequency characteristic which, ideally, is essentially flat, approaching that of white noise. Any deviation from that ideal may result in velocity errors.

Ideally, an MTI filter having a perfectly flat spectral response with a single null at zero would be desirable. Although this is not possible, in the present invention, a mechanization is provided where the MTI filter is connected to an equalizer. The combination filter/equalizer operates such that the stationary (zero velocity) portion of the input signal is first cancelled, and the remaining spectrum is then flattened (in a noise sense, it is whitened); and a very close approximation to the ideal is made.

The equalizer, which may be thought of as a spectral whitening filter, is derived from the inverse response of the MTI filter. The equalizer transfer function then becomes that given in equation (7):

$$W(z) = \frac{1}{H(z)} = \frac{1}{1 - z^{-\tau}} \qquad (7)$$

From a Z-transform analysis of the transfer functions of H(z) and W(z), it may be shown that the resultant pole and zero of the two circuits cancel one another and the resultant frequency response is flat. The difficulty here is the pole location. A pole on the unit circle represents an unstable system and, therefore, should be avoided. If the MTI filter does not perfectly cancel the stationary signal, and when its output signal is applied to the filter equalizer, peaking at the pole location occurs in the frequency response.

This problem is remedied by using a slightly modified transfer function for the equalizer, W(z), and the new transfer function is given in equation (8):

$$W_m(z) = \frac{1}{1 - bz^{-\tau}} \qquad (8)$$

The subscript, m, in equation (8) signifies the modified equalizer and the variable b has the effect of varying the pole position of the equalizer, thereby allowing the extent to which the MTI filter is equalized to be variable, depending upon the clinical application. The range of values for b are $0 < b < 1$.

The difference equation for equation (8) can be obtained by taking the inverse Z transformation of $W_m(z)$, yielding the difference equation given in equation (9):

$$y(n) = x(n) + by(n-\tau) \qquad (9)$$

Figure 15:
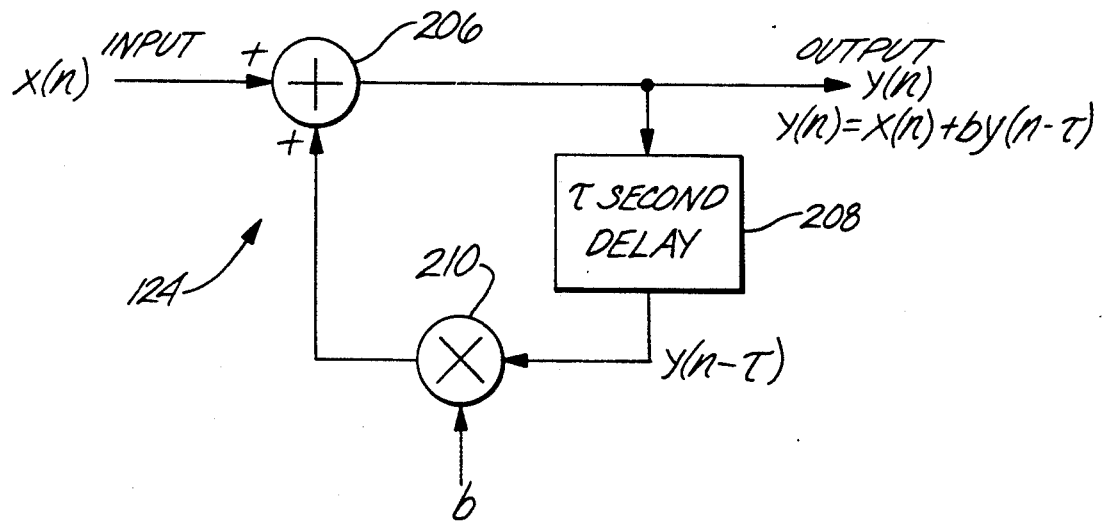
FIG. 15 is a functional block diagram of an equalization filter used in the processor of FIG. 12.

Equation (9) can be implemented using an equalizer 124 having the structure shown in FIG. 15. The input signal x(n) is applied to one input of an accumulator 206. The output of the accumulator 206 is provided to the input of a delay stage 208 similar in function to the delay stage 204 of FIG. 14. The output of the delay stage 208 is multiplied by variable b using multiplier 210. The output of multiplier 210 is added to the input signal x(n) by accumulator 206. The output signal from the accumulator 206 provides the output signal for the equalizer 124.

Figure 16:
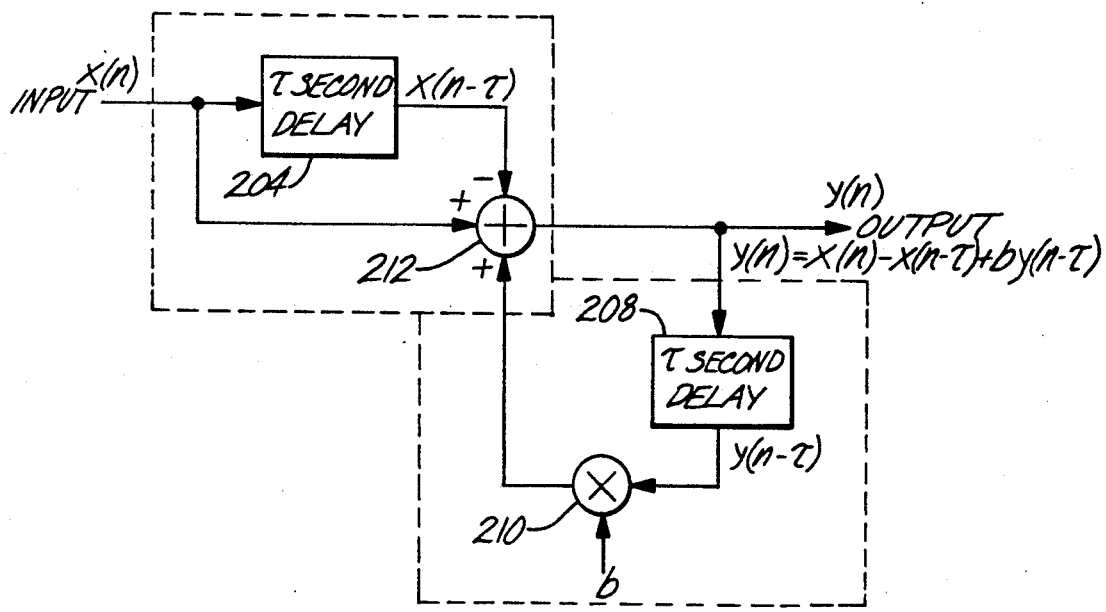
FIG. 16 is a functional block diagram of an MTI filter combined with the equalizer of FIG. 15 and used in the processor system shown in FIG. 12.

The hardware structures for the MTI filter 50, 50' (FIG. 14) and the filter equalizer 124, 124' (FIG. 15) may be combined by connecting the output from the MTI filter to the input of the equalizer. This combination is shown in FIG. 16, where the functions of the accumulators 202 and 206 are combined into a single accumulator 212 to minimize hardware.

The difference equation of the output of the combined network is given in equation (10) and is formed by summing each individual term at the summing junction of 212.

$$y(n) = x(n) - x(n-\tau) + by(n-\tau) \qquad (10)$$

The z domain equivalent of the difference equation of (10) can be found by performing the forward z transformation. The combined response ($H_{combined}$) can then be written as $$H_{combined}(z) = \frac{1 - z^{-\tau}}{1 - bz^{-\tau}} \qquad (11)$$

The combined frequency response of the MTI filter and equalizer may be shown to be extremely flat over the frequency range of interest, which thereby allows the blood flow velocity estimator 56 to make an unbiased estimate. The resultant spectral response of the combined functions maintains a notch at zero velocity, which is representative of a stationary object.

FIG. 12 shows the addition of the equalizer 124, 124' to the Doppler signal processor 120 For both the in-phase and quadrature channels, an equalizer is connected between the output of the corresponding MTI filter 50, 50' and the corresponding input 52, 54 to the velocity estimator 56 of FIG. 3. The MTI filter 50 may be combined with the equalizer 124 as shown in FIG. 16 to eliminate the need for separate accumulators.

It should be noted that, of the n−2 acoustic lines provided to the corresponding MTI filter 50, 50' from the processing circuit 120 during the acquisition of a flow line, one of those acoustic lines is devoted to initializing the delay stage 204 of the MTI filter, and a second one of the acoustic lines is devoted to initializing the delay stage 208 of the equalizer. Hence these two acoustic lines are not processed by the velocity estimator 56. In other words, of n acoustic lines of data input to the processor 120, only n−4 acoustic lines are actually processed by the velocity estimator 56.

As a result of the use of the equalizer of the present invention, the spectral bias which normally occurs in MTI filters is effectively eliminated. The spectrally whitened flow data can then be used by the velocity estimation subsystem without adversely biasing the estimate. The overall results of the equalization scheme allow more accurate velocity estimates regardless of the type of estimator used.

While various embodiments of the invention have been described, it is anticipated that other modifications and adaptations will occur to those skilled in the art upon consideration of this disclosure. Accordingly, the invention is limited only by the appended claims.

What is claimed is:

1. An ultrasonic Doppler flow measuring and imaging system comprising:
   (a) ultrasonic wave transmitting and receiving means for sequentially transmitting a plurality of four or more ultrasonic pulses toward and into a living body at a selected angle over a predetermined time interval and for receiving a corresponding plurality of reflected echo signals, wherein each received echo signal has a tissue motion Doppler component representative of reflection from moving tissue and a blood flow Doppler component representative of reflection from both moving tissue and flowing blood;
   (b) means for processing the plurality of reflected echo signals received during successive predetermined time intervals, the signal processing means including
      (i) means responsive to two or more of the plurality of echo signals (leaving two or more of the plurality of echo signals) for generating a tissue velocity signal representative of the tissue motion Doppler component, and
      (ii) means responsive to the tissue velocity signal for removing the tissue motion Doppler component from the two or more of the plurality of echo signals left to produce tissue velocity compensated signals; and
   (c) means for processing the tissue velocity compensated signals to generate therefrom Doppler flow image data signals for use in imaging the blood flow.

2. Apparatus according to claim 1 in which the generating means includes
   memory means for storing multiple reflected echo signals during each time interval;
   detector means responsive to the memory means for discriminating between those components of the echo signals representative of tissue motion and those representative of the combination of tissue motion and blood flow; and
   velocity estimate means responsive to the detector means for providing a tissue velocity signal indicative of tissue velocity.

3. Apparatus according to claim 2 in which the cancelling means includes demodulator means responsive to the tissue velocity signal and the received echo signals to demodulate the echo signals in a manner which translates the frequency spectrum of the echo signals such that the frequency of the demodulated tissue motion Doppler component of the echo signals is substantially at a baseband frequency corresponding to zero velocity.

4. Apparatus according to claim 3 in which the cancelling means further includes an MTI filter responsive to the demodulator means for removing from the demodulated echo signals those components substantially at the baseband frequency, whereby the MTI filter output signal is representative of the velocity of blood flow.

5. Apparatus according to claim 4 in which the filter output is received by a blood flow velocity estimator and display system.

6. Apparatus according to claim 5 in which the system comprises an ultrasonic Doppler blood flow measuring system and display.

7. Apparatus according to claim 6 in which the imaging system includes color imaging.

8. Apparatus according to claim 3 in which the demodulator means includes multiplier means for multiplying together the tissue velocity signal and the received echo signals.

9. Apparatus according to claim 2 in which the detector means includes amplitude discriminator means for detecting those components of the echo signals which exceed an amplitude threshold.

10. Apparatus according to claim 9 in which the amplitude threshold is adjustable.

11. Apparatus according to claim 1 in which the measuring and imaging system comprises an ultrasonic Doppler blood flow measuring system.

12. Apparatus according to claim 1 in which the signal processing means further includes means for subtracting a stationary bias signal component from the received echo signals to thereby extract from the echo signals a Doppler signal representative of a Doppler component of the received echo signals, and means for thereafter amplifying the Doppler signal to produce a succession of output signals representative of the amplified Doppler components of the reflected echo signals.

13. Apparatus according to claim 1 in which the signal processing means further includes an MTI filter for subtracting a stationary component from the received echo signals to thereby extract from the echo signals a Doppler signal representative of a Doppler component of the received echo signals, and equalization means having a frequency response which is substantially the inverse of the MTI filter and which is responsive to the output of the MTI filter for processing said output to produce an essentially flat frequency response over the range of frequencies being measured.

14. Apparatus according to claim 12 in which the signal processing means further includes an MTI filter for subtracting a stationary component from the received echo signals to thereby extract from the echo signals a Doppler signal representative of a Doppler component of the received echo signals, and equalization means having a frequency response which is substantially the inverse of the MTI filter and which is responsive to the output of the MTI filter for processing said output to produce an essentially flat frequency response over the range of frequencies being measured.

15. A method for producing blood flow representative signals by detecting the Doppler shift of ultrasonic echos having a tissue velocity component and a blood velocity component, the method comprising:
   transmitting a plurality of at least three high frequency ultrasonic pulses into a target along the same line;
   receiving and down converting the frequency of the echoes from the pulses to form echo signals;
   deriving a tissue velocity representative signal from the echo signals of n of the pulses, where n is an integer larger than one;
   combining the tissue velocity representative signal with the echo signals of more than n of the pulses to remove the tissue velocity components therefrom; and
   processing the combined echo signals to generate therefrom Doppler flow image data signals.

16. The method of claim 15, additionally comprising the steps of:
   storing the echo signal from one of the pulses;
   subtracting the echo signals from each of the other pulses from the stored echo signal to form level corrected signals;

amplifying the level corrected signals;
converting the amplified level corrected signals to digital form; and
performing the deriving, combining, and processing steps on the digital signals.

17. The method of claim 16, in which the storing step comprises:
converting the echo signal from the one pulse to digital form to form a digital level correcting signal; storing the level correcting signal in a buffer;
retrieving from the buffer and converting to analog form the level correcting signal in synchronism with the echo signals from each of the other pulses.

18. The method of claim 17, in which the echo signals formed by the receiving and down converting step are in analog form and the subtracting step comprises subtracting the analog echo signals formed by the receiving and down converting step from the retrieved analog level correcting signal.

19. The method of claim 18, in which the amplifying step amplifies the signals produced by the subtracting step.

20. The method of claim 19, in which the processing step comprises:
cancelling the stationary components from the level corrected echo signals and attenuating the high frequency components;
equalizing the level corrected echo signals by boosting the high frequency components, the cancelling and equalizing steps together exhibiting a substantially flat frequency response over the frequency range of the Doppler signal except for a notch at zero frequency; and
processing the equalized signals to form signals representative of the velocity along the line.

21. The method of claim 15, in which the processing step comprises:
cancelling the stationary components from the combined echo signals and attenuating the high frequency components;
equalizing the level corrected echo signals by boosting the high frequency components, the cancelling and equalizing steps together exhibiting a substantially flat frequency response over the frequency range of the Doppler signal except for a notch at zero frequency; and
processing the equalized echo signals to form signals representative of the velocity along the line.

22. The method of claim 21, in which the plurality of ultrasonic pulses comprises at least four pulses, the combined echo signals are in digital form, and the cancelling step comprises delaying the respective echo signals by a time interval equal to the interval between the ultrasonic pulses and subtracting the delayed echo signals from the respective echo signals to form stationary cancelled echo signals.

23. The method of claim 22, in which the equalizing step comprises delaying the respective equalized echo signals by a time interval equal to the interval between the ultrasonic pulses and subtracting the delayed echo signals from the sum of the respective combined echo signals and the respective stationary cancelled echo signals to form the equalized echo signals.

24. The method of claim 23, in which the equalizing step additionally comprises multiplying the delayed echo signals by an adjustable factor that is less than one.

25. The method of claim 15, additionally comprising the steps of:
transmitting a plurality of at least three high frequency ultrasonic pulses along each of a plurality of different lines to insonify a cross sectional area of the target;
forming velocity representative signals for each of the different lines in the manner set forth for the first named line; and
forming a color flow image from the velocity representative signals.

26. The method of claim 15, in which n is two.

27. The method of claim 26, in which the echo signals combined with the tissue velocity representative signal exclude the echo signals from which the tissue velocity representative signal is derived.

* * * * *